US008759401B2

(12) United States Patent
Alam et al.

(10) Patent No.: US 8,759,401 B2
(45) Date of Patent: Jun. 24, 2014

(54) AQUEOUS GEL FORMULATION AND METHOD FOR INDUCING TOPICAL ANESTHESIA

(71) Applicant: Akorn, Inc., Lake Forest, IL (US)

(72) Inventors: Abu Alam, Lake Forest, IL (US); Elias Reichel, Weston, MA (US); Brandon Busbee, Nashville, TN (US)

(73) Assignee: Akorn, Inc., Lake Forest, IL (US)

( * ) Notice: Subject to any disclaimer, the term of this patent is extended or adjusted under 35 U.S.C. 154(b) by 0 days.

(21) Appl. No.: 13/961,453

(22) Filed: Aug. 7, 2013

(65) Prior Publication Data

US 2013/0324612 A1 Dec. 5, 2013

Related U.S. Application Data

(63) Continuation of application No. 13/277,946, filed on Oct. 20, 2011, now abandoned, which is a continuation of application No. 11/491,611, filed on Jul. 24, 2006, now abandoned.

(51) Int. Cl.
*A61K 31/167* (2006.01)
*A61K 9/00* (2006.01)

(52) U.S. Cl.
USPC .......................................... 514/626; 514/613

(58) Field of Classification Search
None
See application file for complete search history.

(56) References Cited

U.S. PATENT DOCUMENTS

| | | | |
|---|---|---|---|
| 2,441,498 A | 5/1948 | Lofgren et al. | |
| 4,039,662 A | 8/1977 | Hecht et al. | |
| 4,174,804 A | 11/1979 | Bosse | |
| 4,470,965 A | 9/1984 | Wolf et al. | |
| 5,340,572 A | 8/1994 | Patel et al. | |
| 5,563,153 A | 10/1996 | Mueller et al. | |
| 5,610,184 A | 3/1997 | Shahinian, Jr. | |
| 5,760,077 A | 6/1998 | Shahinian, Jr. | |
| 5,888,493 A | 3/1999 | Sawaya | |
| 5,972,326 A | 10/1999 | Galin et al. | |
| 6,031,007 A | 2/2000 | Brodin et al. | |
| 6,159,458 A | 12/2000 | Bowman et al. | |
| 6,350,781 B1 | 2/2002 | Shahinia, Jr. | |
| 2001/0006772 A1 | 7/2001 | Goldstein et al. | |
| 2002/0035045 A1 | 3/2002 | Graham et al. | |
| 2005/0059639 A1 | 3/2005 | Wei | |

FOREIGN PATENT DOCUMENTS

| | | |
|---|---|---|
| EP | 0 455 396 B1 | 11/1991 |
| WO | WO 2007/025142 A | 3/2007 |

OTHER PUBLICATIONS

Craig et al., "Refractive index and osmolality of human tears. (Abstract)", Optom Vis Sci. Oct. 1995; 72(10): 718-24.*

Ophthalmology Management, "Focus on Dry Eye Medications", Marketplace, <http://www.ophthalmologymanagement.com/articleviewer.aspx?articleid=86574>, Apr. 1, 2006, p. 1-7.*
"Genteal and Genteal Gel", Novartis Australia, pp. 1-4, <http://www.novartis.com.au/PI_PDF/ged_geg.pdf>, Nov. 2002.*
Akorn, Inc., Lidocaine Hydrochloride Jelly USP, 2%, 1-2 (2003).
Anonymous, "Osmolality and tonicity," 2 pages (Feb. 11, 2007) (downloaded from http://www/ld99.com/reference/notes/text/Osmolality_and_tonicity.html on Apr. 5, 2011).
Astra Zeneca Canada, Inc., Prescribing Information, Xylocaine® Jelly 2% (Lidocaine Hydrochloride Jelly USP) 20 mg/mL, Topical Anesthetic, 1-17 (2004).
Bardocci et al., "Lidocaine 2% gel versus Lidocaine 4% unpreserved drops for topical anesthesia in cataract surgery—A randomized controlled trial," *Ophthalmology*, 110(1): 144-149 (Jan. 2003).
Barequet et al., "Provision of anesthesia with single application of lidocaine 2% gel," *J. Cataract Refract. Surg.*, 25: 626-631 (May 1999).
Bottari et al. "Semisolid ophthalmic vehicles II: Evaluation in albino rabbits of aqueous gel-type vehicles containing Lidocaine and Benzocaine," *Canadian Journal of Pharmaceutical Sciences*, 14(2): 39-43 (1979).
Bozkir et al., "In vitro release study of Lidocaine Hydrochloride from ophthalmic gels containing polyacrylic acid polymers," *Bollettino Chimico Farmaceutico*, 136(8): 550-555 (1997).
Gallemore et al., "High-volume IV injections, in practice," *Review of Ophthalmology News*, 12(12): (Dec. 1, 2005) (downloaded from http://www.revophth.com/index.asp?page=1_859.htm on Jan. 26, 2007).
Gaynes, "Lidocaine gel versus drops." *Ophthalmology*, 110(12): 2429-2430 (Dec. 2003).
Gills et al., "Unpreserved lidocaine to control discomfort during cataract surgery using topical anesthesia," *J. Cataract Refract. Surg.*, 23: 545, 550 (May 1997).
International Bureau of WIPO, International Preliminary Report on Patentability in International Patent Application No. PCT/US2007/0068358 (Feb. 5, 2009).

(Continued)

*Primary Examiner* — Tracy Vivlemore
*Assistant Examiner* — Monica Shin
(74) *Attorney, Agent, or Firm* — Wood, Phillips, Katz, Clark & Mortimer

(57) ABSTRACT

Disclosed is a stable aqueous gel formulation suitable for topical use comprising water, an anesthetic (e.g., lidocaine hydrochloride), a viscoelastic polymer, and a tonicity modifier, wherein the aqueous gel formulation is free of preservatives and phosphate buffer, is isotonic with physiological fluids, and is sterile and has low particulate count. Also disclosed is a method of inducing topical anesthesia on a tissue or organ, e.g., the eye, of an animal comprising providing a stable aqueous gel formulation comprising water, an anesthetic, a viscoelastic polymer, and a tonicity modifier, wherein the aqueous gel formulation is free of preservatives and phosphate buffer, is isotonic with physiological fluids, and is sterile, and topically administering an effective amount of the aqueous gel formulation to the tissue or organ of the animal.

9 Claims, No Drawings

(56) References Cited

OTHER PUBLICATIONS

Jacobi et al., "A Comparative Study of Topical vs Rerobulbar Anesthesia in Complicated Cataract Surgery," *Arch. Ophthalmol.*, 118: 1037-1043 (Aug. 2000).

Koch, "Efficacy of Lidocaine 2% jelly as a topical agent in cataract surgery," *J. Cataract Refract. Surg.*, 25: 632-634 (May 1999).

Kozak et al., "Lidocaine gel anesthesia for intravitreal drug administration," *Retina, The Journal of Retinal and Vitreous Diseases*, 25(8): 994-998 (2005).

Kwok et al., "Efficacy of lignocaine gel for outpatient laser treatment in inflamed eyes," *Eye*, 15: 608-611 (2001).

Lang et al., "Design and evaluation of ophthalmic pharmaceutical products," in: *Modern Pharmaceutics*, Edition 4 (Banker et al., eds.), Chapter 13, 415 (2002).

Levy et al., Lidocaine hypersensitivity after subconjunctival injection, *Canada Journal of Ophthalmology*, 41: 204-206 (2006).

Liang et al., "Toxicity of intraocular Lidocaine and Bupivacaine," *American Journal of Ophthalmology*, 125(2): 191-196 (1998).

Novartis Australia, "Genteal® and Genteal® Gel," 1-4 (Nov. 2002) Retrieved from http://www.novartis.com.au/PI_PDF/ged_geg.pdf.

Oksuz et al., "Efficacy of Lidocaine 2% gel in pterygium surgery", *Acta Ophthalmologica Scandinavica*, 83(2): 206-209 (2005).

Paavola et al., "Controlled release of Lidocaine from injectable gels and efficacy in rat sciatic nerve block," *Pharmaceutical Research*, 12(12): 1997-2002 (1995).

Rebolleda et al., "Comparison of Lidocaine 2% gel versus retrobulbar anesthesia for implantation of Ahmed glaucoma drainage," *Acta Ophthalmologica Scandinavica*, 83(2): 201-205 (2005).

Ricci et al., "Rheological characterization of poloxamer 407 Lidocaine hydrochloride gels," *Pharmaceutical Research*, 17(3): 161-167 (2002).

RXMED, "Xylocaine® Jelly 2%," 1-8 (Jan. 2003) Retrieved from http://www.rxmed.com/b.main/b2.pharmaceutical/b2.1.monographs/CPS-%20Monographs/CPS-%20(General%20Monographs-%20X)/XYLOCAINE%20JELLY.html.

Sautou-Miranda et al., "Impact of deep freezing on the stability of 25 mg/ml Vancomycin ophthalmic solutions," *International Journal of Pharmaceutics*, 234: 205-212 (2002).

Serrato et al., "The lens-coating agent and the electroretinogram," *Documenta Ophthalmologica*, 106: 225-230 (2003).

Shin et al., "Development of Lidocaine gels for enhanced local anesthetic action," *International Journal of Pharmaceutics*, 287(1-2): 73-78 (2004).

Soliman et al., "Comparative clinical trial of topical anesthetic agents in cataract surgery: Lidocaine 2% gel, Bupivacaine 0.5% drops, and Benoxinate 0.4% drops," *J. Cataract Refract. Surg.*, 30: 1716-1720 (Aug. 2004).

Thill et al., "Lidocaine gel versus combined topical anesthesia using Bupivacaine, Osybuprocaine and Diclofenac eyedrops in cataract surgery," *Ophthalmologica*, 219(3): 167-170 (2005).

Yu et al., "Comparison of Lidocaine 2% gel versus Amethocaine as the sole anesthetic agent for strabismus surgery," *Ophthalmology*, 110(7): 1426-1429 (Jul. 2003).

* cited by examiner

AQUEOUS GEL FORMULATION AND METHOD FOR INDUCING TOPICAL ANESTHESIA

BACKGROUND OF THE INVENTION

Anesthesia is a process commonly used to block the perception of pain. The first public demonstration of administering an anesthetic agent occurred over 150 years ago when diethyl ether was utilized during a surgical operation to remove a tumor. Today, anesthetic agents are utilized in patient procedures across the medical specialties.

Anesthetic agents are used in procedures carried out on various tissues and organs. For example, with regard to procedures performed on the eye, common anesthetic agents utilized include subconjunctival injections of aqueous lidocaine and tetracaine drops. However, subconjunctival injections of aqueous lidocaine are less than desirable as many patients suffer from anxiety caused by needle phobia and/or the physical pain caused by the actual injection. Indeed, it is believed that the anxiety levels can reach the point where patients avoid the necessary medical care. The topical administration of tetracaine drops avoids these needle-related problems. However, there are some drawbacks with such drops. Some of the drops administered to patient may miss the eye due to the shaking of the hand or the blinking of the eye. The residence time of the drop on the eye is limited, for example, less than about a minute. Thus, the anesthetic efficacy of the tetracaine drops could become insufficient since both the onset of anesthesia is not rapid, and the duration of anesthetic activity is limited. Some of the formulations reported to be sterile do not specify the particle size limits. In addition, tetracaine may also be toxic to the cornea. Thus, there is a desire for other, more efficacious anesthetic formulations for topical administration, especially formulations which cause less anxiety, pain, and provide both rapid onset and prolonged anesthetic activity.

The invention provides such an anesthetic formulation. These and other advantages of the invention, as well as additional inventive features, will be apparent from the description of the invention provided herein.

BRIEF SUMMARY OF THE INVENTION

The foregoing need has been fulfilled to a great extent by the invention which provides an aqueous gel formulation comprising water, an anesthetic, a viscoelastic polymer, and a tonicity modifier. Specifically, the invention provides an aqueous gel formulation which comprises, consists essentially of, or consists of, water, an anesthetic, a viscoelastic polymer, and a tonicity modifier. The formulation may also contain a pH adjusting agent or a product produced as a result of pH adjustment. Advantageously, the gel formulation is free of preservatives and/or phosphate buffer. The aqueous gel formulation of the invention is targeted for application to various tissues or organs (internal or external) of an animal, particularly to the eye. The invention also provides a method for inducing topical anesthesia to a tissue or organ of an animal. The administration of the topical formulation of the invention preferably avoids the need to administer a subsequent administration (e.g., topical or injection) of the anesthetic during a medical procedure.

DETAILED DESCRIPTION OF THE INVENTION

The invention provides, in an embodiment, an aqueous gel formulation comprising water, an anesthetic, a viscoelastic polymer, and a tonicity modifier, wherein the anesthetic is present in an amount of 15 mg per ml to about 50 mg per ml of the formulation, wherein the aqueous gel formulation is free of preservatives and phosphate buffer, is isotonic with physiological fluids, and is sterile having less than about 100 particles of 50 microns particle size or more per ml of the aqueous gel formulation.

The aqueous gel formulation of the invention is free of preservatives, e.g., methyl paraben, propyl paraben, or EDTA. It is also free of phosphate buffer. The aqueous gel formulation of the invention is contemplated for use on various internal and external organs of the body or tissue, particularly on the eye. In an embodiment, the gel formulation is also free of permeation enhancers such as skin permeation enhancers, e.g., glycols, surfactants, or bile salts.

In another embodiment, the invention provides an aqueous gel formulation comprising water, an anesthetic, a viscoelastic polymer, and a tonicity modifier, wherein the anesthetic is present in an amount of 25 mg per ml to about 38 mg per ml of the formulation, and is suitable for topical administration to the eye. The aqueous gel formulation is free of preservatives and phosphate buffer, is isotonic with physiological fluids, and is sterile having less than about particles of 50 microns particle size or more per ml of the aqueous gel formulation.

In accordance with the invention, any suitable anesthetic can be used. Suitable anesthetics include lidocaine, bupivicaine, mepivicaine, proparacaine, and narcaine, and pharmaceutically acceptable salts thereof. Pharmaceutically acceptable salts are those derived from such organic and inorganic acids such as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, benzoic, and similarly known acceptable acids. Preferably, the anesthetic is lidocaine hydrochloride.

In certain embodiments, the aqueous gel formulation comprises an anesthetic in an amount of 15 mg per ml to 38 mg per ml of the formulation. Typically, the aqueous gel formulation comprises an anesthetic in an amount of 20 mg per ml to 35 mg per ml of the formulation, preferably, in an amount of 25 mg per ml to 30 mg per ml of the foimulation, and more preferably, in an amount of about 35 mg per ml of the formulation.

The viscoelastic polymer comprises any suitable gelling agent. Suitable gelling agents include hydroxypropylmethylcellulose, methylcellulose, sodium carboxymethyl cellulose, ethylene oxide/propylene oxide copolymers, alginates, hyaluronates, guaran, pectin, tragacanth, carubin, carrageenan, and polyacrylic acid. Preferably, the gelling agent is hydroxypropylmethylcellulose.

The aqueous gel formulation can have any suitable pH. A suitable pH includes from about 5.0 to about 7.5, preferably, from about 5.5 to about 7.0, and more preferably, from about 6.0 to about 6.5. The pH is adjusted to minimize local, focal point irritation. The aqueous gel formulation may contain an acid or base used to adjust the pH, or any reaction product formed as a result of pH adjustment.

The aqueous gel formulation can have any suitable viscosity to enable drop-wise administration to the eye, for example, from about 2000 to about 10,000 cps, preferably from about 5000 to about 8000 cps, at 25° C. An advantage of the formulation of the invention is that, in view of the viscous nature of the formulation, the residence time of the formulation on the tissue or organ, e.g., the eye, of the patient is increased compared to anesthetic solutions which are less viscous. The increased residence time translates to long lasting anesthetic activity.

The aqueous gel formulation includes any suitable tonicity modifier to match the osmolarity (mosm) of the physiological fluids. Suitable tonicity modifiers include sodium chloride, potassium chloride, mannitol, sucrose, lactose, fructose, maltose, dextrose, dextrose anhydrous, propylene glycol and glycerol. Preferably, the tonicity modifier is sodium chloride. The tonicity modifier can be present in an amount of from about 0.5 to about 1% by weight, preferably from about 0.8 to about 1% by weight, of the gel formulation. For example, the tonicity modifier, particularly sodium chloride, can be present in an amount of 0.9% by weight of the aqueous gel formulation. Typically, the aqueous gel formulation has a tonicity of from about 250 to about 350 mosm, particularly about 280 mosm. The tonicity helps to avoid hyper/hypo tonicity effects on the tissue or organ, particularly on the corneal layer, thereby increasing patient comfort.

The aqueous gel formulation can be prepared by any suitable method. For example, an aqueous solution containing the desired quantity of the viscoelastic polymer (gelling agent) and an aqueous solution containing the desired quantity of the anesthetic agent, the tonicity modifier, and pH adjusting agent, can be prepared separately. The solution containing the anesthetic and other ingredients can be sterile filtered on a 0.2 micron filter. The solution containing the viscoelastic polymer (gelling agent) is sterilized, e.g., by ethylene oxide or gamma radiation. The two solutions can be combined and mixed, and if desired diluted, to obtain an embodiment of the aqueous gel formulation of the invention.

Another aspect of the invention is a method of inducing topical anesthesia on a tissue or organ of an animal. The method comprises (a) providing an aqueous gel formulation comprising water, an anesthetic, a viscoelastic polymer, and a tonicity modifier, wherein the anesthetic is present in an amount of 15 mg per ml to about 50 mg per ml of the formulation, wherein the gel formulation is free of preservatives and phosphate buffer, is isotonic with physiological fluids, and is sterile having less than about 100 particles of 50 microns particle size or more per ml of the aqueous gel formulation; and (b) topically administering an effective amount of the aqueous gel formulation to the tissue or organ of the animal; whereby anesthesia is induced on the tissue or organ of the animal. The aqueous gel formulation can be administered in any suitable manner. For example, it can be administered drop-wise from a dropper, by a cotton-tipped applicator, or by a caulking gun or similar device.

In an embodiment, the invention provides a method of inducing topical anesthesia on the eye of an animal comprising providing an aqueous gel formulation comprising water, an anesthetic, a viscoelastic polymer, and a tonicity modifier, wherein the anesthetic is present in an amount of 25 mg per ml to 38 mg per ml of the formulation, and suitable for topical administration to the eye; and topically administering an effective amount of the aqueous gel formulation to the eye of the animal; whereby anesthesia is induced on the eye of the animal.

In any of the embodiments, upon topical administration of the aqueous gel formulation of the invention to the tissue or organ of the animal, anesthesia onsets within 5 minutes, e.g., within about 15 seconds to about 3 minutes of administration, particularly within about 5 seconds to about 1 minute of administration, or more particularly within about one second to about 30 seconds of administration. The onset time, particularly on the eye, is independent of the concentration of the anesthesia.

Anesthesia induced on the tissue or organ after administration of the aqueous gel formulation lasts up to 30 minutes or more, e.g., up to about 10 to 30 minutes, up to about 15 to 20 minutes, or up to about 25 minutes, so as to permit completion of a lengthy procedure, for example, cataract surgery. The duration of activity is dependent upon the concentration of the anesthetic. For example, the duration is 30 minutes or more at 3.5%; 20 minutes or more at 2.5%, and 10 minutes or more at 1.5% concentration of the anesthetic by weight. The embodiments of the invention possess advantageous properties including rapid onset of topical anesthesia and prolonged anesthetic activity, enabling various medical and surgical procedures to proceed without undesirable intervention, e.g., an anesthetic injection.

Embodiments of the aqueous gel formulation of the invention possess long term storage stability, for example, they are stable for a period of up to 1, 2, 3 months or more, e.g., 24 months or more, at 40° C. and 20% relative humidity (RH). The aqueous gel formulation of the invention possesses freeze/thaw stability. The aqueous gel formulation of the invention advantageously has long term stability such that the assay of the anesthetic is within 95.0% to 105.0%; not more than 0.1% large anesthetic degradents (particularly large lidocaine degradent); and not more than 1.0% of total anesthetic degradents (particularly total lidocaine degradent) over 3 months at 40° C. and 20% RH. The degradents can be measured by any suitable method, e.g., HPLC. In embodiments of the invention, particularly where lidocaine hydrochloride is used on the eye, the aqueous gel formulation is clear, colorless, and free or substantially free from undissolved material or particulates.

Embodiments of the aqueous gel formulation of the invention have the advantage of decreased risk of post-surgical endophthalmitis and/or decreased corneal toxicity. It is contemplated that the formulation of the invention provides a superior anesthetic property over 0.5% tetracaine, and does not require a subconjunctival injection prior to treatment with intravitreal injection. In addition, lidocaine is less toxic to the cornea than tetracaine.

As the aqueous gel formulation of the invention is free of preservatives and is targeted for single use, it provides for increased patient safety. There is a decreased probability of cross contamination and irritation on the tissue or organ, particularly on the corneal/epithelial layer of the eye. Preservatives, such as parabens, tend degrade, e.g., hydrolyze to the corresponding acid (p-hydroxybenzoic acid) and alcohols (e.g., methanol, ethanol, or propanol). Since the formulation is free of preservatives, the possibility of degradents being present in the formulation is decreased, and therefore, any adverse effect due to such degradents is decreased. Advantageously, the time to onset of anesthetic activity is independent of concentration of the anesthetic. The duration of anesthetic activity can be controlled by controlling the concentration of the anesthetic. Advantageously, the aqueous gel formulation of the invention contains the anesthetic and the viscoelastic polymer in a dissolved molecular state, thereby permitting constant rate of release of the anesthetic over time. This leads to increased duration of anesthetic activity and patient comfort. In addition, controlling the particle size of impurities and their number as well as reducing degradents to a minimum increases corneal safety.

The aqueous gel formulation of the invention is contemplated for use on procedures carried out on various tissues and organs, e.g., in bronchoscopy, colonoscopy, GI procedures, intubation, dentistry, ear, nose, and throat (ENT), urology, and gynecology.

The aqueous gel formulation of the invention can be filled for single use in any suitable size container, for example, 5 ml dropper bottles, using aseptic techniques.

The following examples further illustrate the invention but, of course, should not be construed as in any way limiting its scope.

EXAMPLE 1

This example illustrates a method of preparing an aqueous gel formulation comprising lidocaine hydrochloride in an amount of 15 mg per ml of the formulation in accordance with an embodiment of the invention.

500 ml of purified water is charged into a sterile vessel #1 using an aseptic technique. 25 g of sterile hydroxypropylmethylcellulose is charged into vessel #1 using an aseptic technique and mixed. In a separate vessel #2, 15 g of lidocaine hydrochloride and 9 g of sodium chloride are dissolved in about 400 ml of purified water and passed through a 0.2 micron filter and aseptically transferred to vessel #1 with mixing. Hydrochloric acid and/or sodium hydroxide solutions are filtered through a 0.2 micron filter and added to vessel #1 to adjust the pH to 6.0-6.5. Purified water is passed through a 0.2 micron filter to bring the formulation to 1 kg. The formulation is a sterile viscous gel and may be filled into sterile unit dose bottles of suitable size, e.g., 5 ml dropper bottles, using aseptic technique.

EXAMPLE 2

This example illustrates a method of preparing an aqueous gel formulation comprising lidocaine hydrochloride in an amount of 25 mg per ml of the formulation in accordance with an embodiment of the invention.

500 ml of purified water is charged into a sterile vessel #1 using an aseptic technique. 25 g of sterile hydroxypropylmethylcellulose is charged into vessel #1 using an aseptic technique and mixed. In a separate vessel #2, 25 g of lidocaine hydrochloride and 9 g of sodium chloride are dissolved in about 400 ml of purified water and passed through a 0.2 micron filter and aseptically transferred to vessel #1 with mixing. Hydrochloric acid and sodium hydroxide solutions are filtered through a 0.2 micron filter and added to vessel #1 to adjust pH 6.0-6.5. Purified water is passed through a 0.2 micron filter to bring the formulation to 1 kg. The formulation is a sterile viscous gel and may be filled into sterile unit dose bottles of suitable size, e.g., 5 ml dropper bottles, using aseptic technique.

EXAMPLE 3

This example illustrates a method of preparing an aqueous gel formulation comprising lidocaine hydrochloride in an amount of 35 mg per ml of the formulation in accordance with an embodiment of the invention.

500 ml of purified water is charged into a sterile vessel #1 using aseptic technique. 25 g of sterile hydroxypropylmethylcellulose is charged into vessel #1 using aseptic technique and mixed. In a separate vessel #2, 35 g of lidocaine hydrochloride and 9 g of sodium chloride are dissolved in about 400 ml of purified water and passed through a 0.2 micron filter and aseptically transferred to vessel #1 with mixing. Hydrochloric acid and sodium hydroxide solutions are filtered through a 0.2 micron filter and added to vessel #1 to adjust pH 6.0-6.5. Purified water is passed through a 0.2 micron filter to bring the formulation to 1 kg. The formulation is a sterile viscous gel and may be filled into sterile unit dose bottles of suitable size, e.g., 5 ml dropper bottles, using aseptic technique.

EXAMPLE 4

This example illustrates the long term stability and freeze/thaw stability of an embodiment of the aqueous gel formulation of the invention comprising lidocaine hydrochloride in an amount of 15 mg per ml of the formulation.

An aqueous gel formulation comprising lidocaine hydrochloride in an amount of 15 mg per ml of the formulation is placed on accelerated stability storage at 40° C. and 20% relative humidity. The lidocaine hydrochloride formulation and potential degradents are measured initially and after 1, 2, and 3 months of accelerated storage using a high pressure liquid chromatographic method. There is no change of the formulation characteristics, assay values, and degradents upon accelerated storage supporting a room temperature stability of 24 months. The freeze thaw cycle data also show the formulation to be stable during transportation and extreme seasonal exposures to temperatures. The stability data is shown in Table 1.

TABLE 1

Stability data for aqueous gel formulation

| Test | Limits | Initial | 1 mo. | 2 mo. | 3 mo. | Freeze/thaw |
|---|---|---|---|---|---|---|
| Assay: Lidocaine Hydrochloride | 95.0%-105.0% | 99.7% | 100.4% | 99.6% | 98.0% | 97.1% |
| Large Lidocaine Degradent | NMT: 0.1% | 0.06% | 0.07% | 0.06% | 0.07% | 0.08% |
| Total Lidocaine Degradent | NMT: 1.0% | 0.06% | 0.07% | 0.06% | 0.07% | 0.08% |
| Minimum Fill | NLT: 5 ml | 6.3 ml | 6.2 ml | 6.2 ml | 6.2 ml | 6.3 ml |
| pH | 5.5-7.5 | 6.3 | 6.0 | 5.9 | 5.8 | 6.0 |
| Appearance | Clear, colorless solution; free from undissolved material | Pass | Pass | Pass | Pass | Pass |
| Sterility | Sterile | Pass | N/A | N/A | N/A | N/A |

EXAMPLE 5

This example illustrates the long term stability and freeze/thaw stability of an embodiment of the aqueous gel formulation of the invention comprising lidocaine hydrochloride in an amount of 25 mg per ml of the formulation.

An aqueous gel formulation comprising lidocaine hydrochloride in an amount of 25 mg per ml of the formulation is placed on accelerated stability storage at 40° C. and 20% relative humidity. The lidocaine hydrochloride formulation and potential degradents are measured initially and after 1, 2, and 3 months accelerated storage using a high pressure liquid chromatographic method. There is no change of the formulation characteristics, assay values and degradents upon accelerated storage supporting a room temperature stability of 24 months. The freeze thaw cycle data also show the formulation to be stable during transportation and extreme seasonal exposures to temperature. The stability data is shown in Table 2.

TABLE 2

Stability data for aqueous gel formulation

| Test | Limits | Initial | 1 mo. | 2 mo. | 3 mo. | Freeze/thaw |
|---|---|---|---|---|---|---|
| Assay: Lidocaine Hydrochloride | 95.0%-105.0% | 99.3% | 100.6% | 101.1% | 98.7% | 98.3% |
| Large Lidocaine Degradent | NMT: 0.1% | 0.06% | 0.07% | 0.08% | 0.06% | 0.07% |
| Total Lidocaine Degradent | NMT: 1.0% | 0.07% | 0.07% | 0.08% | 0.06% | 0.14% |
| Minimum Fill | NLT: 5 ml | 6.5 ml | 6.4 ml | 6.4 ml | 6.4 ml | 6.5 |
| pH | 5.5-7.5 | 6.4 | 6.0 | 6.0 | 5.9 | 6.1 |
| Appearance | Clear, colorless solution; free from undissolved material | Pass | Pass | Pass | Pass | Pass |
| Sterility | Sterile | Pass | N/A | N/A | N/A | N/A |

EXAMPLE 6

This example illustrates the long term stability of an embodiment aqueous gel formulation of the invention comprising lidocaine hydrochloride in an amount of 35 mg per ml of the formulation.

An aqueous gel formulation comprising lidocaine hydrochloride in an amount of 35 mg per ml of the formulation is placed on accelerated stability storage at 40° C. and 20% relative humidity. The lidocaine hydrochloride and potential degradents are measured initially and after 1, 2, and 3 months accelerated storage using a high pressure liquid chromatographic method. There is no change of the formulation characteristics, assay values and degradents upon accelerated storage supporting a room temperature stability of 24 months. The freeze thaw cycle data also show the formulation to be stable during transportation and extreme seasonal exposures to temperature. The stability data is shown in Table 3.

TABLE 3

Stability data for aqueous gel formulation

| Test | Limits | Initial | 1 mo. | 2 mo. | 3 mo. | Freeze/thaw |
|---|---|---|---|---|---|---|
| Assay: Lidocaine Hydrochloride | 95.0%-105.0% | 98.9% | 100.1% | 100.4% | 98.9% | 98.5% |
| Large Lidocaine Degradent | NMT: 0.1% | 0.05% | 0.07% | 0.07% | 0.06% | 0.05% |
| Total Lidocaine Degradent | NMT: 1.0% | 0.05% | 0.07% | 0.07% | 0.06% | 0.09% |
| Minimum Fill | NLT: 5 ml | 6.4 ml | 6.4 ml | 6.3 ml | 6.3 ml | 6.4 |
| pH | 5.5-7.5 | 6.3 | 6.0 | 6.0 | 5.9 | 6.1 |
| Appearance | Clear, colorless solution; free from undissolved material | Pass | Pass | Pass | Pass | Pass |
| Sterility | Sterile | Pass | N/A | N/A | N/A | N/A |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An aqueous gel formulation consisting of water, lidocaine hydrochloride, a viscoelastic polymer, and sodium chloride, wherein the lidocaine hydrochloride is present in an amount of 35 mg per ml of the formulation and the sodium chloride is present in an amount of 9 mg per ml of the formulation, wherein the aqueous gel formulation has a viscosity of 2000 to 10,000 cps at 25° C., is free of preservatives and phosphate buffer, has an osmolality of 250 to 350 mOsm/kg, and is sterile having less than about 100 particles of 50 microns particle size or greater per ml of the aqueous gel formulation, wherein the viscoelastic polymer is hydroxypropylmethylcellulose, the pH of the aqueous gel formulation is from 5.0 to 7.0, and the aqueous gel formulation is suitable for administration to the eye of an animal.

2. A method of inducing topical anesthesia in the eye of an animal comprising:
    (a) providing an aqueous gel formulation according to claim 1 and
    (b) topically administering an effective amount of the aqueous gel formulation to the eye of the animal;
    whereby anesthesia is induced on the eye of the animal.

3. The method of claim 2, wherein the anesthesia onsets within 5 minutes of administration of the aqueous gel formulation.

4. The method of claim 2, wherein the anesthesia lasts up to 30 minutes or more.

5. The aqueous gel formulation of claim 1, which is packaged in a unit dose container.

6. The aqueous gel formulation of claim 1, whose pH is from 5.5 to 7.0.

7. The aqueous gel formulation of claim 1, whose pH is from 5.5 to 6.5.

8. The aqueous gel formulation of claim 1, whose pH is from 6.0 to 6.5.

9. The aqueous gel formulation of claim 5, wherein the unit dose container is a dropper bottle.

\* \* \* \* \*